(12) United States Patent
Durand et al.

(10) Patent No.: US 11,540,771 B2
(45) Date of Patent: Jan. 3, 2023

(54) DETERMINING A STATE OF A SOLID TUMOR BASED ON NEURAL ACTIVITY WITHIN THE SOLID TUMOR

(71) Applicant: CASE WESTERN RESERVE UNIVERSITY, Cleveland, OH (US)

(72) Inventors: Dominique M. Durand, Cleveland, OH (US); Grant McCallum, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 446 days.

(21) Appl. No.: 16/623,088

(22) PCT Filed: Jun. 25, 2018

(86) PCT No.: PCT/US2018/039293
§ 371 (c)(1),
(2) Date: Dec. 16, 2019

(87) PCT Pub. No.: WO2018/237384
PCT Pub. Date: Dec. 27, 2018

(65) Prior Publication Data
US 2020/0214628 A1 Jul. 9, 2020

Related U.S. Application Data

(60) Provisional application No. 62/523,816, filed on Jun. 23, 2017.

(51) Int. Cl.
*A61N 1/36* (2006.01)
*A61B 5/00* (2006.01)
*A61N 1/05* (2006.01)
*A61B 5/24* (2021.01)

(52) U.S. Cl.
CPC .............. *A61B 5/4839* (2013.01); *A61B 5/24* (2021.01); *A61B 5/4029* (2013.01);
(Continued)

(58) Field of Classification Search
CPC ......... A61B 5/24; A61B 5/4842; A61B 5/686; A61B 5/6847; A61B 5/4836;
(Continued)

(56) References Cited

FOREIGN PATENT DOCUMENTS

WO 2016/199142 A1 12/2016

OTHER PUBLICATIONS

Borovikova, Lyudmila V., et al. "Vagus nerve stimulation attenuates the systemic inflammatory response to endotoxin" Nature 405.6785 (2000): 458-462.
(Continued)

*Primary Examiner* — Jon Eric C Morales
(74) *Attorney, Agent, or Firm* — Tarolli, Sundheim, Covell & Tummino LLP

(57) ABSTRACT

One aspect of the present disclosure relates a method of diagnosis and/or treatment of a solid tumor. The method includes directly measuring neural activity within a solid tumor for a time and determining a state of the solid tumor based on the neural activity. The diagnosis and/or treatment can be determined based on the state of the solid tumor. In some instances, the neural activity can be used in a closed loop to detect the neural activity, determine the state, determine the risk, apply treatment, check again for neural activity, and cease treatment when the neural activity is gone.

16 Claims, 19 Drawing Sheets

(52) U.S. Cl.
CPC ............ *A61B 5/4842* (2013.01); *A61B 5/686* (2013.01); *A61N 1/0551* (2013.01); *A61N 1/36002* (2017.08); *A61N 1/36139* (2013.01)

(58) Field of Classification Search
CPC ... A61B 5/4029; A61B 5/4058; A61B 5/4064; A61N 1/36002; A61N 1/36
See application file for complete search history.

(56) References Cited

OTHER PUBLICATIONS

Huang, Di, et al. "Nerve fibers in breast cancer tissues indicate aggressive tumor progression." Medicine 93.27 (2014).

Li, Sha, Yanlai Sun, and Dongwei Gao. "Role of the nervous system in cancer metastasis." Oncology letters 5.4 (2013): 1101-1111.

Gidron, Yori, Hugh Perry, and Martin Glennie. "Does the vagus nerve inform the brain about preclinical tumours and modulate them?." The lancet oncology 6.4 (2005): 245-248.

Cain, David M., et al. "Functional interactions between tumor and peripheral nerve: changes in excitability and morphology of primary afferent fibers in a murine model of cancer pain." Journal of Neuroscience 21.23 (2001): 9367-9376.

Pundavela, Jay, et al. "Nerve fibers infiltrate the tumor microenvironment and are associated with nerve growth factor production and lymph node invasion in breast cancer." Molecular oncology 9.8 (2015): 1626-1635.

PCT International Search Report for corresponding International Application Serial No. PCT/US2018/039293, dated Sep. 6, 2018, pp. 1-17.

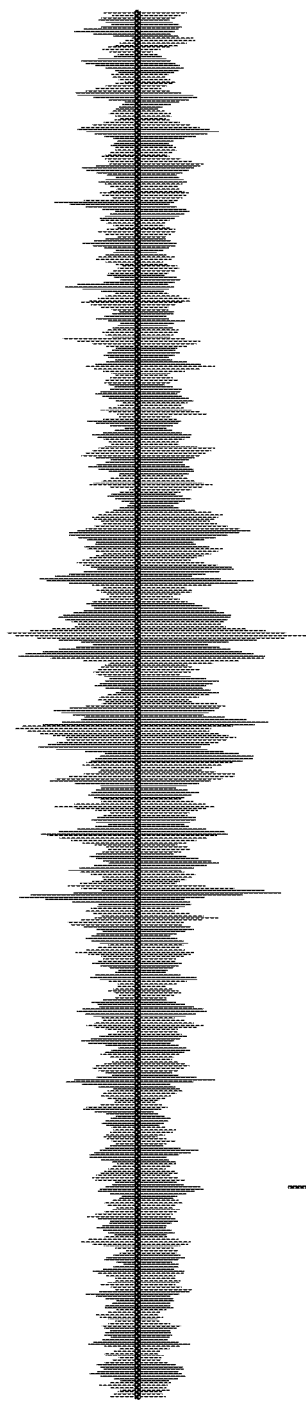
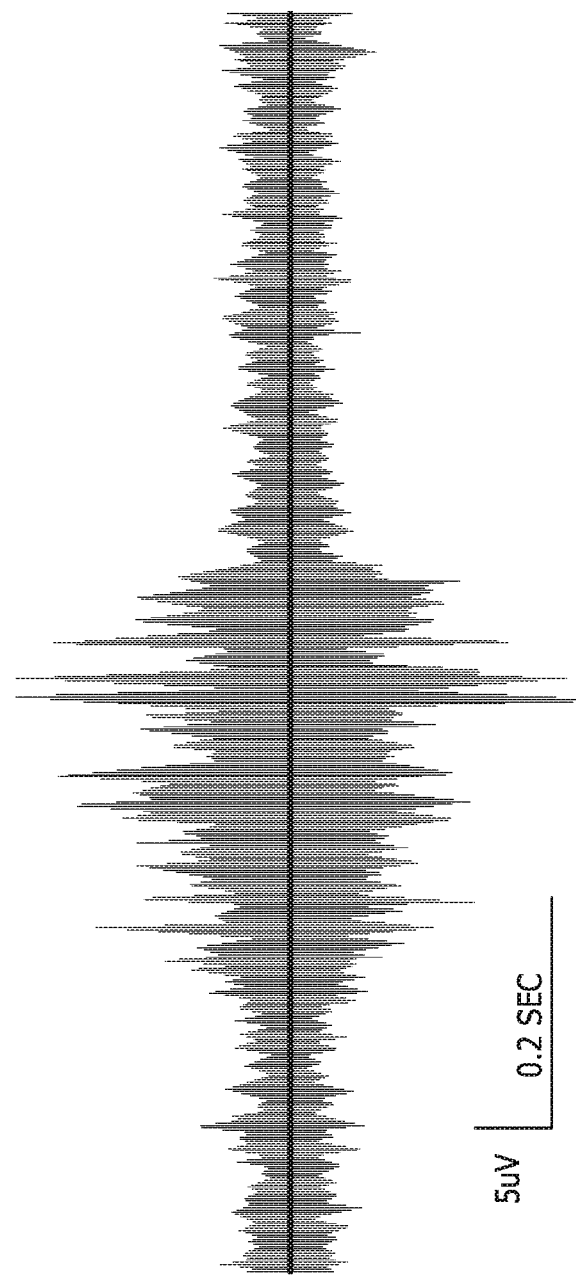

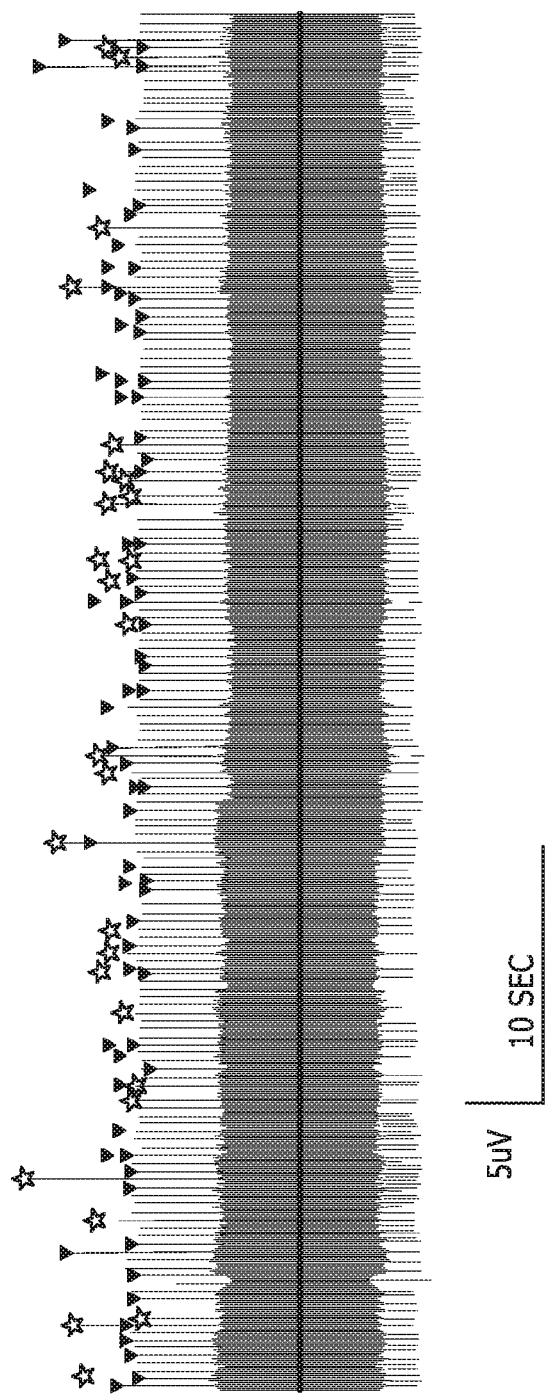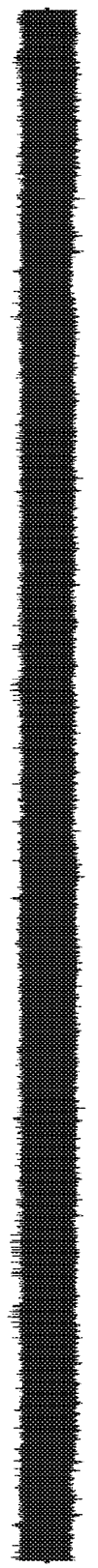
FIG. 12
FIG. 13

US 11,540,771 B2

DETERMINING A STATE OF A SOLID TUMOR BASED ON NEURAL ACTIVITY WITHIN THE SOLID TUMOR

CROSS-REFERENCE TO RELATED APPLICATION

This application claims priority to U.S. Provisional Application Ser. No. 62/523,816, filed Jun. 23, 2017, entitled "TUMOR NERVE INTERFACE", the entirety of which is hereby incorporated by reference for all purposes.

TECHNICAL FIELD

The present disclosure relates generally to neural activity within a solid tumor and, more specifically, to systems and methods that determine a state of a solid tumor based on the neural activity within the solid tumor.

BACKGROUND

A solid tumor is an abnormal mass of tissue that usually does not contain cysts or liquid areas. Solid tumors, which can be benign (not cancer), pre-malignant, or malignant (cancer), can be found in the brain, ovary, breast, colon, prostate, pancreas, and other tissues. A malignant solid tumor in the breast can be referred to as breast cancer.

Breast cancer is a global problem, accounting for nearly a quarter of all cancers in women worldwide. It is estimated that as many as 1.7 million women are diagnosed with breast cancer every year. One in eight women will be diagnosed with breast cancer during her lifetime. An estimated 90% of deaths due to breast cancer are a consequence of metastatic disease, whether the cancer was metastatic at diagnosis or a metastatic recurrence developed later. Permanent treatments to eradicate metastasis do not exist. In fact, there is no cure once metastatic disease has occurred. The median survival with metastatic breast cancer is three years, and that number has had no statistically significant change in over twenty years.

SUMMARY

The present disclosure relates generally to neural activity within a solid tumor and, more specifically, to systems and methods that determine a state of a solid tumor based on the neural activity within the solid tumor. For example, the state of the solid tumor can be benign or cancerous. When the solid tumor in the cancerous state, a risk of growth and/or a risk of metastasis can be determined based on comparing at least a portion of the neural activity to one or more neural signal metrics. Treatment can be suggested and/or performed based on the state and/or the determination of the associated risks.

In one aspect, the present disclosure can include a method for determining a state of a solid tumor based on neural activity within the solid tumor. The method can include directly measuring neural activity within the solid tumor for a time. The measuring can be done by a recording device. The method can also include determining the state of the solid tumor based on the neural activity. The determining can be done by a system comprising a processor.

In another aspect, the present disclosure can include a system that can determine a state of a solid tumor based on the neural activity within the solid tumor. The system can include a recording electrode coupled to a computing device. The recording electrode can be configured to record neural activity within the solid tumor for a time. The computing device can include a non-transitory memory and a processor to receive the neural activity and determine the state of the solid tumor based on the neural activity.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 9-10 show a burst of EMG activity originating from the control that contaminates the tumor recording;

FIG. 12 shows neural activity within the tumor before lidocaine injection;

FIG. 13 shows neural activity within the tumor post lidocaine injection;

DETAILED DESCRIPTION

I. Definitions

Figure 1:
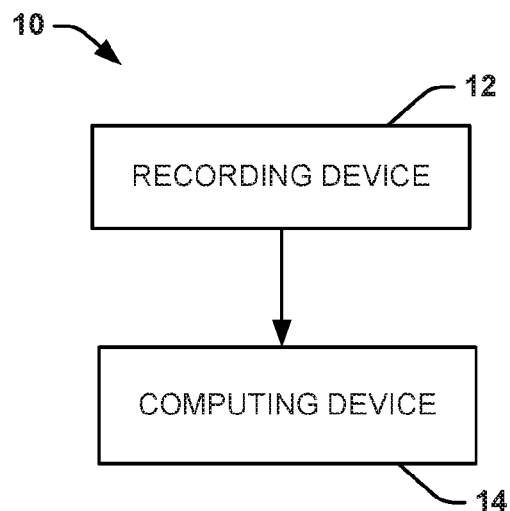
FIG. 1 is a schematic diagram showing a system that determines a state of a solid tumor based on neural activity detected within the solid tumor in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the term "solid tumor" can refer to an abnormal mass of tissue that usually does not contain cysts or liquid areas. Solid tumors, which can be benign (not cancer) or malignant (cancer), can be found in the brain, ovary, breast, colon, prostate, pancreas, and other tissues.

As used herein, the term "neural activity" can refer to detectable conduction within a nerve (e.g., an autonomic nerve, which experiences autonomic activity). In some instances, the conduction can be electrical conduction. When not otherwise modified, the term "activity" can refer to "neural activity". The neural activity can include one or more neural signals that include one or more properties or characteristics.

As used herein, the term "state" can refer to a particular condition that something is in at a particular time. For example, the state of a solid tumor can be one of benign (not cancer) or malignant (cancer); in some instances, the state can be pre-cancer. A solid tumor with a state of malignant can be associated with a risk of growth and/or a risk of metastasis. In some instances, the state may be "requires further testing" to determine whether the solid tumor is benign or malignant.

As used herein, the term "metastasis" can refer to the development of a secondary malignant growth at a distance from a primary malignant solid tumor.

As used herein, the term "growth" can refer to the process of increasing in physical size. Tumor growth can refer to the process of the tumor increasing in physical size.

As used herein, the term "neural signal metric" can refer to a quantifiable measure of a property of a neural signal. The neural signal metric can be used (often in combination with one or more thresholds) to predict a risk of growth and/or a risk of metastasis. For example, the neural signal metric can be based on a shape of the neural signal, a number and/or amplitude of spike events in the neural activity for the time, power, entropy, complexity, and/or mean number of crossings of the neural activity within the solid tumor for the time, and/or one or more frequency characteristics of the neural activity within the solid tumor for the time.

As used herein, the term "recording device" can refer to any type of measuring instrument that records or detects a signal. Examples of recording devices can include a recording electrode, magnetic field detector, etc.

As used herein, the term "electrode" can refer to a conductor through which electricity enters or leaves an object, substance, or region.

As used herein, the term "nerve" can refer to a group of one or more fibers (or "neurons" that employ electrical and chemical signals to transmit motor, sensory, and/or autonomic information from one body part to another.

As used herein, the term "autonomic nervous system" can refer to a part of the nervous system responsible for control of the bodily functions that acts largely unconsciously. The autonomic nervous system includes parasympathetic neurons and sympathetic neurons.

As used herein, the term "treatment" can refer to a session of medical care or the administration of a dose of medicine for a certain duration and at a certain time. For example, the treatment of the solid tumor can include delivering a pharmaceutical to the solid tumor, delivering a therapeutic agent to the solid tumor, delivering an immunotherapy to the solid tumor, stimulating neural activity to or from the tumor, blocking neural activity to or from the tumor, delivering radiation to the solid tumor, or the like.

As used herein, the term "threshold" can refer to a magnitude that must be exceeded for a certain result to be achieved.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

Neural fibers are known to infiltrate solid tumors and establish a direct connection between the nervous system and tumor cells. It was long believed that these neural fibers did not engage in meaningful neural activity. However, the neural activity of these neural fibers is actually quite meaningful so that the present disclosure relates generally to detection and usage of this neural activity within a solid tumor. The neural activity in a solid tumor for a time can be directly measured by a recording device that can be proximal to the solid tumor or within the solid tumor. A state of the solid tumor can be determined based on the neural activity.

A closed loop system can be created using the systems and methods of the present disclosure. The neural activity within a solid tumor can be directly measured and a state of the solid tumor can be determined. For example, the state can be benign, malignant, or requires further testing. Determining the state based on the neural activity creates a new diagnostic mechanism for the solid tumor. When the tumor is in the malignant state, a risk of growth and/or a risk of metastasis can be determined based on comparing one or more properties of characteristics of the neural activity signal to a neural signal metric. Treatment can be delivered at a certain dose and/or at a certain time to the solid tumor based on the risk of growth and/or the risk of metastasis. The loop can continue with checking again for the neural activity. The treatment can be ceased when the neural activity is gone. The detected neural activity can also contribute to the development of new treatment protocols and preventative measures.

III. Systems

One aspect of the present disclosure can include a system 10 (FIG. 1) that can that determine a state of a solid tumor based on neural activity detected within the solid tumor. The system 10 can include at least a recording device 12 and a computing device 14. The recording device 12 can be configured to record neural activity within the solid tumor for a time. The computing device 14 can receive the neural activity from the recording device 12 and determine a state of the solid tumor based on the neural activity.

The recording device 12 can be configured in a manner that permits detection of the neural activity within the tumor. The neural device can be one or more electrodes, a device that detects a magnetic field corresponding to the neural activity, or the like (e.g., any bioelectric recording device that can record the neural activity within the tumor and be connected to an amplifier). As one example, the recording device 12 can be implemented as a sheet that can be laid over at least a portion of the tumor. In another example, the recording device 12 can be configured for implantation within the solid tumor (outside the nerve). As a further example, the recording device 12 can be an intrafascicular electrode that is configured for insertion within a nerve located within or associated with the solid tumor. The intrafascicular electrode can be implanted within a nerve that innervates an organ that currently includes or once included the solid tumor.

Until recently, it had been impossible to record chronic, intrafascicular activity in peripheral nerves due to electrode size and rigidity. However, using highly flexible materials technology the electrode size and rigidity barrier has been overcome. As an example, an intrafascicular electrode can be made that includes a 10 micron diameter carbon nanotube (CNT) yarn electrode and a custom ultra-low noise recording system. Other materials can be used as long as the flexural rigidity of the material approximates that of the nerve targeted for implantation.

The recording device 12 can be coupled to the computing device 14 to send the detected neural activity for analysis. The coupling can be according to a wired connection in some instances. In other instances, the coupling can be according to a wireless connection. In still other instances, the coupling can be according to both a wired connection and a wireless connection.

Figure 2:
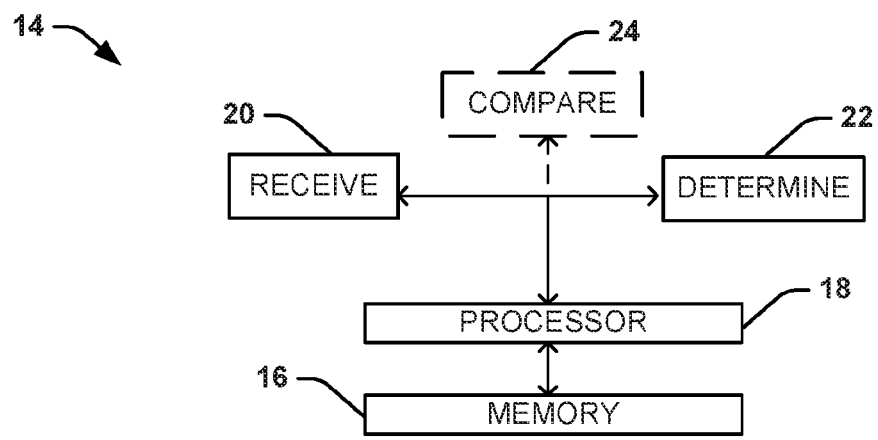
FIG. 2 is a schematic diagram of the computing device in FIG. 1.

The computing device 14 is shown in more detail in FIG. 2. As shown in FIG. 2, the computing device 14 includes a non-transitory memory 16 and a processor 18. As shown, the non-transitory memory 16 and the processor 18 can be hardware devices within the computing device 14. The non-transitory memory 16 can store instructions and the processor 18 can access the instructions within the non-transitory memory 16 and execute the instructions. The instructions can include receive 20 the neural activity from the recording device 12 and determine 22 a state of the solid tumor based on the neural activity.

In some instances, when the solid tumor is known to exist, the state can be benign or malignant. A third state can be pre-cancer. The determination of the state can lead to the system 10 being used as a diagnostic tool. The system 10, in some instances, can output a diagnosis that includes the determined state of the tumor.

The state can be determined based on a detection of the neural activity. In other words, the existence of neural activity from within the solid tumor may be an indicator that the solid tumor may be or is malignant. To further determine the state, the neural activity can be compared to one or more neural signal metrics. For example, the neural signal metrics can be based on a shape of the neural signal, a number and/or amplitude of spike events in the neural activity for the time, power, entropy, complexity, mean number of crossings, etc. of the neural activity within the solid tumor for the time, one or more frequency characteristics of the neural activity within the solid tumor for the time, or the like.

In other instances, when a solid tumor has been removed from an organ, a potential recurrence of the solid tumor can be detected based on the presence of neural activity. This indication of neural activity can be used to determine if further testing should take place. For example, based in the neural activity, a physician can order a biopsy or other confirming test.

When the solid tumor has been characterized as malignant, the computing device 14 can compare 24 one or more properties or characteristics of the neural signal within the neural activity to one or more neural signal metrics (which can be based on a shape of the neural signal, a number and/or amplitude of spike events in the neural activity for the time, power, entropy, complexity, and/or mean number of crossings of the neural activity within the solid tumor for the time, and/or one or more frequency characteristics of the neural activity within the solid tumor for the time). The comparison can be used to determine a risk of growth or a risk of metastasis based on a property of the neural activity exceeding one or more thresholds. For example, when the malignant solid tumor is melanoma, when a rate of change of a neural signal within the neural activity is high, indicating a fast growing tumor, the risk of growth and/or metastasis would be high. The processor 18 can create an output recommending delivery of a treatment to the solid tumor based on the risk of growth and/or a risk of metastasis.

As another example, a treatment can be delivered to the solid tumor based on a property of the neural activity. The treatment can include delivering a pharmaceutical to the solid tumor, delivering a therapeutic agent to the solid tumor; delivering an immunotherapy to the solid tumor, stimulating neural activity to or from the tumor, blocking neural activity to or from the tumor, and/or delivering radiation to the solid tumor. Based on the comparison, it can be determined if and when (e.g., a specific time) to apply the treatment to the solid tumor. The processor 18 can create an output recommending delivery of a treatment to the solid tumor according to the determination. For example, the output can set forth a time course for the treatment to be delivered based on the determination.

In some instances, the system 10 can includes a treatment delivery device (not shown). The treatment delivery device can communicate with the computing device 14 and/or a user associated with the computing device 14. The treatment delivery device can be configured to perform the recommended delivery of the treatment to the solid tumor based on the output from the computing device 14. In some instances, the treatment delivery device can be an intravenous access device. In other instances, the treatment delivery device can include one or more radioactive delivery sources. In further instances, the treatment delivery device can include a heat source. In other instances, the treatment delivery device can include a radio frequency (RF) source.

In some instances, the system 10 can engage in a closed loop control of the delivery of treatment to the tumor. When the neural activity is detected by the recording device 12, the computing device 14 can determine the state of the solid tumor to be malignant. The computing device 14 can then determine the risk of the solid tumor growing or becoming metastatic. Treatment can then be applied to the solid tumor using the treatment delivery device. The system 10 can then check again for the neural activity. The treatment can be ceased when the activity is gone.

IV. Methods

Figure 3:
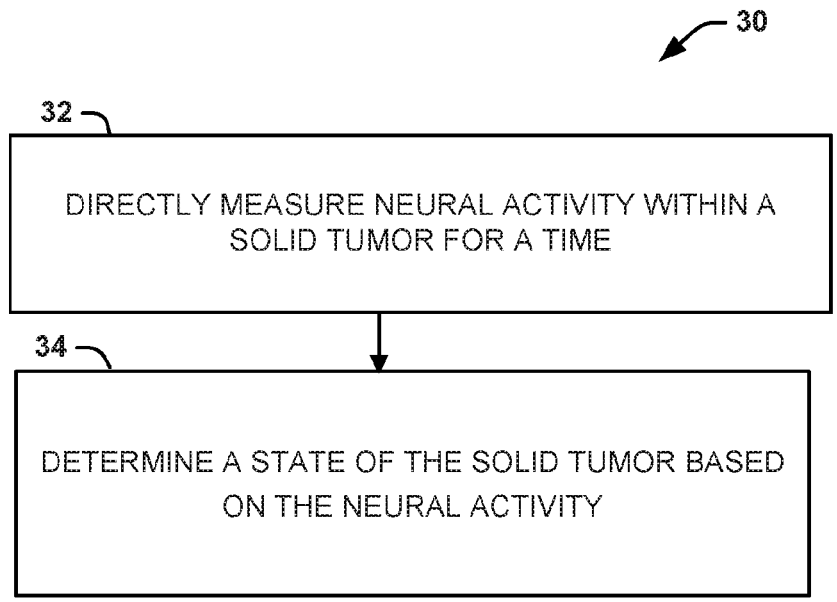
FIG. 3 is a process flow diagram illustrating a method for determining a state of a solid tumor based on neural activity detected within the solid tumor according to another aspect of the present disclosure.
Figure 4:
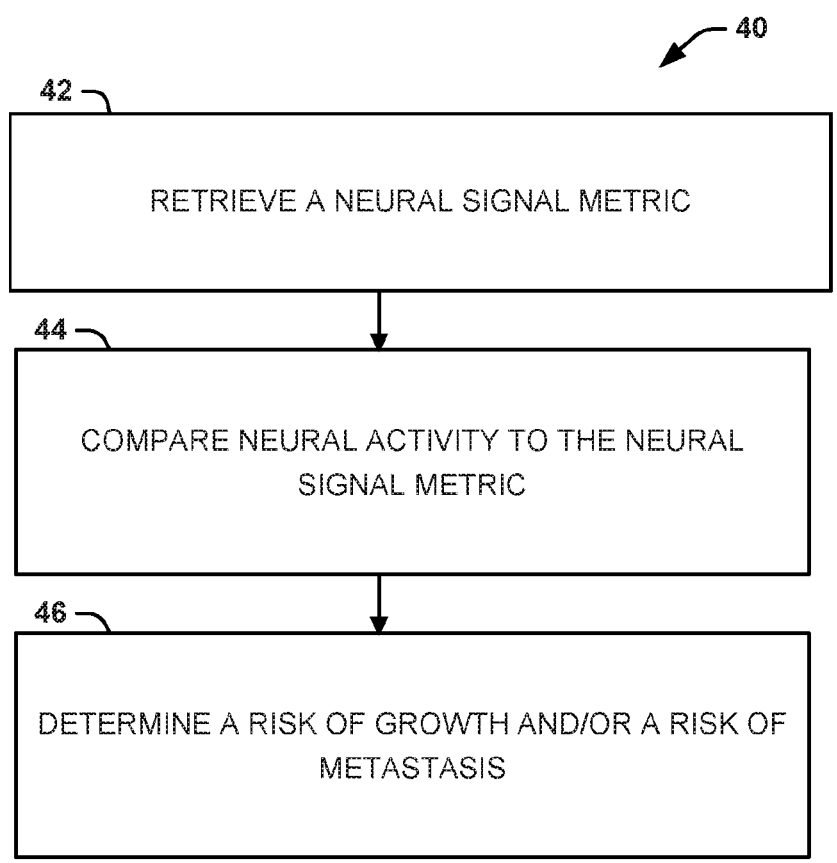
FIG. 4 is a process flow diagram illustrating a method for determining a risk of growth and/or a risk of metastasis based the neural activity detected using the method of FIG. 3.
Figure 5:
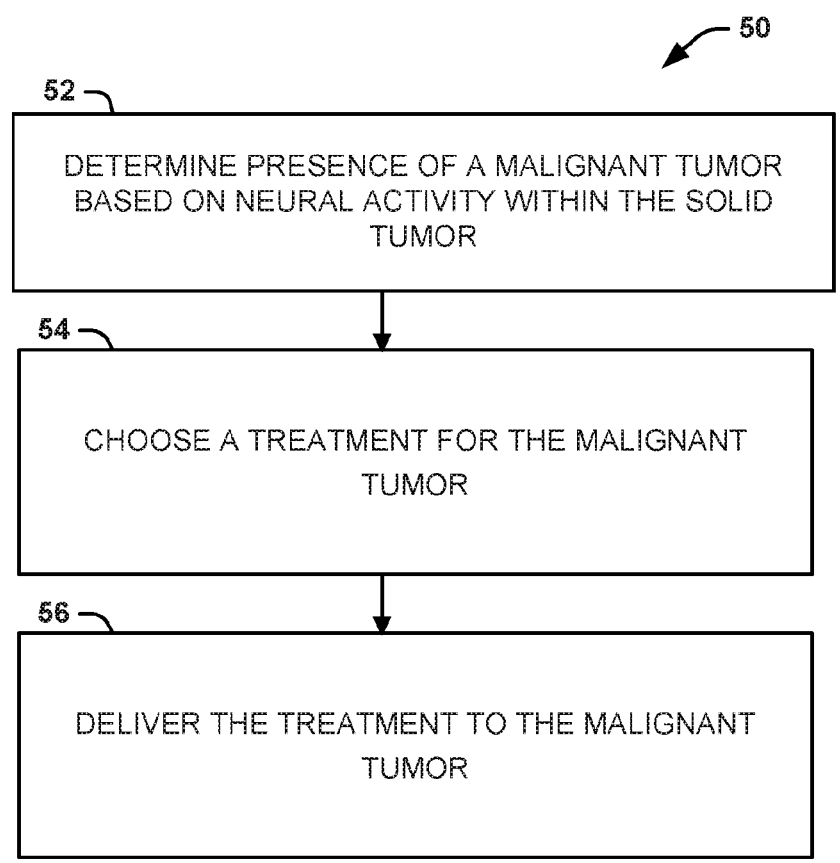
FIG. 5 is a process flow diagram illustrating a method for treating a solid tumor based on the neural activity detected using the method of FIG. 3.

Another aspect of the present disclosure can include methods 30-50 that can be performed by the system 10 shown in FIG. 1. FIG. 3 shows a method 30 for determining a state of a solid tumor based on neural activity detected within the solid tumor. FIG. 4 shows a method 40 for determining a risk of growth and/or a risk of metastasis based the neural activity detected using the method of FIG. 3. FIG. 5 shows a method 50 for treating a solid tumor based on the neural activity detected using the method of FIG. 3.

The methods 30-50 are illustrated as process flow diagrams with flowchart illustrations. For purposes of simplicity, the methods 30-50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30-50.

Referring now to FIG. 3, illustrated is a method 30 for determining a state of a solid tumor based on neural activity detected within the solid tumor. At Step 32, neural activity within a solid tumor can be directly measured (e.g., by recording device 12). At Step 34, a state of the solid tumor can be determined (e.g., by computing device 14) based on the neural activity. For example, the state of the solid tumor can be benign or malignant. However, the state can also be pre-cancer or needs further testing. The state can be malignant when the neural activity is detected in the tumor.

Referring now to FIG. 4, illustrated is a method 40 for determining a risk of growth and/or a risk of metastasis based the neural activity detected using the method of FIG. 3. At Step 42, a neural signal metric can be retrieved (e.g., from non-transitory memory 16). At Step 44, the neural activity can be compared to the neural signal metric (e.g., by processor 18). At 46, a risk of growth and/or a risk of metastasis can be determined (e.g., by processor 18). The risk can be based on the neural activity satisfying one or more thresholds.

Referring now to FIG. 5, illustrated is a method 50 for treating a solid tumor based on the neural activity detected using the method of FIG. 3. At Step 52, the presence of a malignant tumor can be detected (by computing device 14) based on neural activity within the solid tumor (detected by a recording device 12). At Step 54, a treatment for the malignant tumor can be chosen (by the computing device 14 and/or by a user associated with the computing device 14). At Step 56, the treatment can be delivered (by a treatment delivery device) to the malignant tumor.

In some instances, the treatment can be delivered under a closed loop control. When the neural activity is detected by the recording device 12, the computing device 14 can determine the state of the solid tumor to be malignant. The computing device 14 can then determine the risk of the solid tumor growing or becoming metastatic. Treatment can then be applied to the solid tumor using the treatment delivery device. The system 10 can then check again for the neural activity. The treatment can be ceased when the activity is gone.

V. Example

The following example is for the purpose of illustration only is not intended to limit the scope of the appended claims.

This example demonstrates the direct measurement of neural activity in a solid tumor (a breast tumor in a 4T1 mouse model). Based on this neural activity metastasis can be determined with 95% confidence if the number of spike events exceeds a predetermined threshold such as 150 per a given 10 minute recording period. Additionally, it may be possible to predict metastasis based on the activity of specific populations of nerve fibers within the tumor.

Methods

Surgery

Female mice were inoculated with 4T1 breast cancer in the lower left quadrant of the abdomen. The lateral length and width of the surface tumor were measured and recorded daily utilizing digital micro-calipers. The implantation surgery was conducted within 7 to 10 days after inoculation; the approximate time in which the tumor reaches 0.5 cm×0.5 cm in size. This is the minimum size necessary for differential electrodes to be implanted 5 mm apart, the ideal distance for micro recordings. At this distance both differential electrodes could record from the central mass of the tumor by minimizing interference from common mode signals. The implant device had 3 main components: electrodes, connector port and recording system. There were 5 electrodes (2 sets of differential electrodes, and one ground electrode), a transcutaneous connector port to which the electrodes were soldered and woven into a Dacron mesh for stability, and the INTAN recording system for daily measurements.

During surgery, the 6 prong connector port was implanted into the back (dorsal side) of the mouse. For recording from an area of interest such as an inervated tumor, or other highly enervated area a DFT (Drawn Filled Tubing) based electrode was utilized. This design interface should be more physically flexible compared to cuff electrodes, and is capable to be implanted into an area of interest and record from multiple neural sites at once. DFT electrodes also induce less of an immune response than cuff electrodes, thus maintaining impedance longer, and can be utilized for chronic recordings without risk of biocompatibility related degradation and malfunction. The two sets of differential DFT electrodes were tunneled from the back of the mouse to the lower left quadrant of the abdomen; one set of electrodes was implanted in the breast cancer tumor approximately 5 mm apart, the other was placed on the opposite side of the abdomen as a control. A ground wire was tunneled down the back of the mouse. The implant port was secured by suturing the attached Dacron mesh to the back muscles and epidermis to prevent the possibility the subject could irritate or explant the port during recovery or the subsequent chronic trial. After one day of recovery daily monopolar and differential recordings were conducted with the subject under 1.5 isoflurane for approximately 1 hour each day. Impedance of the electrodes was also measured daily to ensure that the implanted electrodes were functioning as intended.

As a control, 3 mice were inoculated with D2A1 cells. D2A1 is a slow growing, but aggressive, triple negative tumor with a low rate of metastasis (rate of metastasis 3-8%). The mice were imaged and recorded every other day for 42 days. The mice were then perfused and the tumors explanted for histology. It has been found previously that nerves only grow in metastatic tumors and not in the tissue is found in non-metastatic tumors. A non-metastatic tumor is the ideal null hypothesis test to ensure that any activity found in the metastatic tumors are neural.

Recording

The main instruments of recording was the INTAN recording system, utilized with two custom INTAN amplifier circuit boards with 16 and 32 channels for monopolar and differential recordings respectively. The subjects were anesthetized for recordings under 1.75-2% Isoflurane. The percutaneous ports were connected to the INTAN amplifier boards (either monopolar or differential) once the subject was anesthetized. The analog signals from the tumor, control, and ground electrodes were sampled at 20 ksps, the hardware-averaged across the channels and filtered between 500-1000 Hz. Baseline recordings during surgery were obtained during 5-20 minutes periods to ensure that the electrodes were placed properly. After two days of recovery recording were obtained daily for one hour (30 minutes duration monopolar, 30 minutes duration differential). The impedance of the implanted electrodes was measured daily, post implantation, at a sampling frequency of 1000 Hz to ensure their functionality.

The neural signals from the tumor electrodes are recorded simultaneously on 16 channels which are hardware averaged to decrease Johnson noise from the electrode and amplifier. Additionally the signal is filtered between 500-1000 Hz to remove additional sources of noise. To ensure that no noise was being produced by the recording system a shake test was performed. This test involves isolating and moving each point of the recording setup and the animal while monitoring for increased noise or signal artifact on all channels. At the end of the recording trials, perfusion was performed on the subject to explant the tumor for histology.

Vagus Stimulation

At the end of the daily recording trials, a terminal experiment was conducted on two mice (one pre and one post metastasis), where the vagus nerve was exposed, separated from the surrounding muscle structure, and elevated and supported on two hook electrodes approximately 1 mm apart in order to see if there is a neural response in the tumor. The vagus nerve was stimulated (with forward and reverse polarity) with an electrical waveform generator at 5 mA amplitude with a 100 µSec PW stimulation at 0.25 Hz. Five trials were conducted per mouse, each trial lasting approximately 30 seconds, with a 3-minute break between trials. The response in the tumor and control were recorded by the Intan System. A 10-minute baseline recording was taken prior to stimulation.

These experiments were designed to test whether a large action potential impulse induced in the vagus nerve will travel to the supposedly recruited nerves in the primary tumor and create a measurable action potential. In these trials, forward and reverse polarity impulses were administered to the vagus nerve in order to avoid electrical artifacts from being mistakenly classified as neural action potentials in the primary tumor.

Lidocaine Experiment

The lidocaine experiment was designed to test the neural nature of the signals identified during the chronic recordings. Lidocaine is a common nerve blocker, which inhibits neurons from creating an action potential by blocking fast voltage gated Na+ channels in the neuronal cell membrane responsible for signal propagation. At the termination of 5 chronic recording experiments a final 30-minute bassline recording was taken, then 0.5 mL of Lidocaine 2% was injected into the tumor. Recordings continued for 30 minutes post lidocaine injection. If the baseline activity seen during the chronic recordings ceased after the lidocaine injection, this would be a strong indication that the signals recorded within the tumor are indeed neural.

To counter the possibility that the injection process, or the salt in the lidocaine, could potentially short-circuit the electrodes, an additional experiment was performed whereby before the injection of Lidocaine, 0.5 mL of saline was injected into the tumor. There was a continuous recording for 30 minutes before and after the injection. No change in recorded activity during this control experiment will indicate that any decrease in signal during the lidocaine experiment is a result of a blocking in neural activity, instead of a chemical or mechanical phenomenon.

Data Analysis

The recordings were processed via lowband filtering and spike sorting Matlab programs to determine the trend of neural activity over time. The primary recordings used in analysis were the differential recordings. The monopolar recordings were utilized in case either one of the differential electrodes failed.

In order to determine if neural activity occurred, the differential lowband recordings from the tumor and control sides were both filtered by the same program, and the threshold for neural activity was found. The threshold was set to 2.5 time the baseline RMS (Root Mean Squared) of the signal; this is to determine if the counted spikes were neural.

The number of spikes with an amplitude greater that the threshold was counted. Neural spikes, recorded within the tumor that shared the same time marker to a spike above threshold in the control were excluded from the final neural spike count to eliminate obvious artifacts. To ensure that this motion artifact did not contaminate the tumor spike counting, the tumor activity was disregarded during any instance the control activity was above threshold.

UltraMegaSort 2000

To organize and classify the recorded neural activity, the spike sorting algorithm UltraMegaSort 2000 ("UMS2k") was applied to the filtered neural signal. The neural spikes are divided into clusters; these clusters were then analyzed for their relative firing rate over time, throughout tumor growth and metastasis. An important metric UMS2k uses during classification is refractory period violations (rpv). Rpvs are spikes that are classified into a cluster despite occurring within the refractory period of a neuron of another spike grouped in that same cluster; there should be a minimal number of rpvs in low noise neural recordings.

Imaging

The 4T1 cells utilized in this trial have been genetically modified to have the D-luciferin protein marker. This allows the 4T1 cells to bind to luciferase and bioluminescence for approximately 30 minutes. Utilizing bioluminescence imaging (BLI) the tumors' growth and metastasis can be monitored. For the 4T1 mouse model, metastasis is anticipated to occur between days 19-22 after inoculation. Post inoculation the mice were subject to BLI imaging every other day until day 17; following this time, the mice were imaged daily.

SPECTRUM BLI machine was utilized for imaging. Each mouse was administered 0.1 mL of luciferase via IP injection. Seven minutes after the injection (when the luciferase is attached to the tumor cells and bioluminescence is at peak brightness) the mice were imaged at two exposure times. Once at an auto exposure and once at a 1-minute exposure time, to ensure that the maximum number of photons were captured from the 4T1 cells without oversaturating the image.

After the SPECTRUM imaging, the images were processed. Two ROIs (regions of interest) were selected, a 3 cm×3 cm ROI over the tumor site, and one 3 cm×2 cm ROI over the lungs. The photons collected within each ROI were processed, and utilized to determine the tumor size, as well as cell migration and metastasis in the lungs.

Histology

In order to determine the presence of nerve fibers within the breast cancer tissue, histology was performed. The mice were perfused and the primary tumor mass extracted and fixed in formalin. Utilizing immunofluorescence staining for autonomic nerve fibers (Cholinergic VACh-T, and Sympathetic TH) the tumor specimens were evaluated. The formalin-fix tissue samples from the 4T1 breast cancer tumors were sectioned into 40-um thick slices. Slices were selected from three main areas of the tumor: adjacent to the skin, center of the tumor mass, and adjacent to the abdominal wall.

Immunostaining was performed (TH staining-rabbit anti rabbit to stain for sympathetic fibers, and VACh-T—Sheep anti goat to stain for cholinergic fibers.) according to the manufacturer's instructions. The slides were also stained with DAPI to identify the nuclei of the cancer cells. Any distinct voids within the DAPI staining will identify a potential area of interest during imaging, as a void means a lack of cancer cells, due to necrosis, blood vessel growth, or nerve growth.

Results

Impedance Test

To ensure the continuous functionality of the implanted electrodes, impedance measurements were performed daily. A sharp increase in impedance indicates the electrodes failed, while a gradual increase is consistent with post implantation fibrous encapsulation. For all the trials the electrodes have remained functional.

Figure 6:
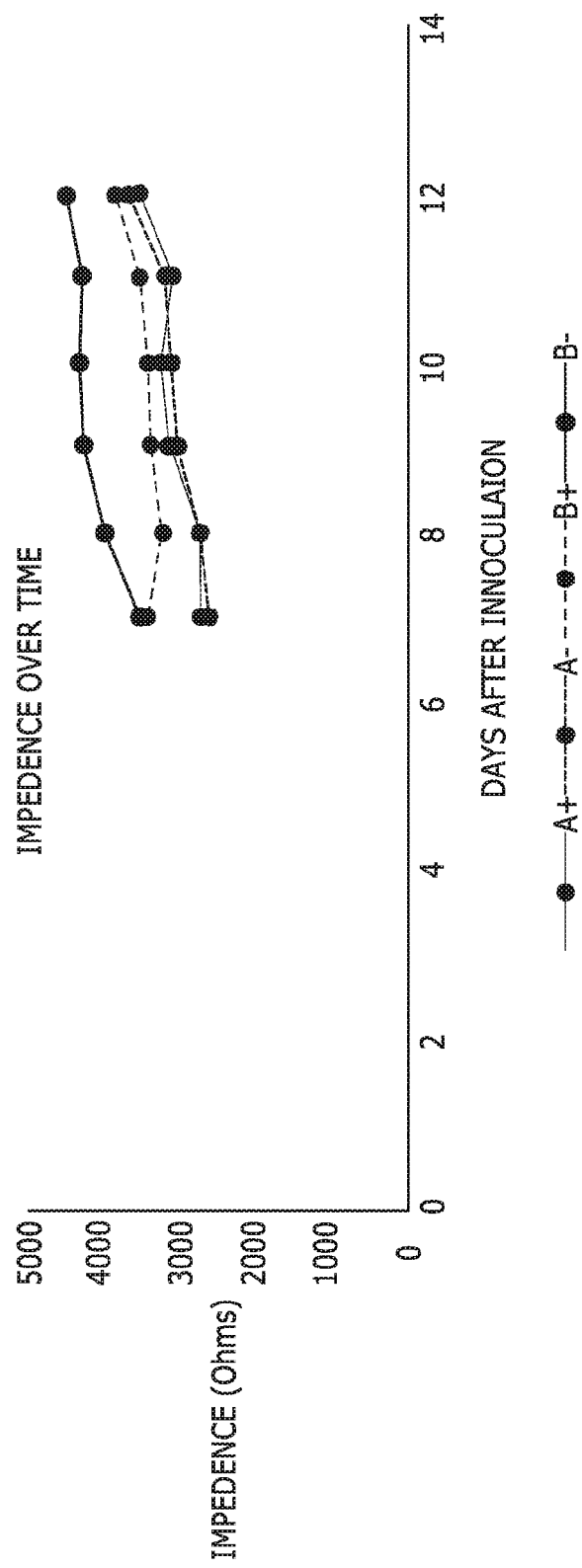
FIG. 6 is a plot of impedance change over time post implantation from the day of implantation until the day of termination in four implanted electrodes.

FIG. 6 is a representative graph of the impedance over the recording period. (+/−A are the differential electrodes in the tumor, +/−B are the differential electrodes in the Control). The graph shows the expected increase of impedance over time for the DFT electrodes with fibrous encapsulation. These measurements were consistent across all of the recording trials.

Neural Recording in Tumor and Control

Figure 7:
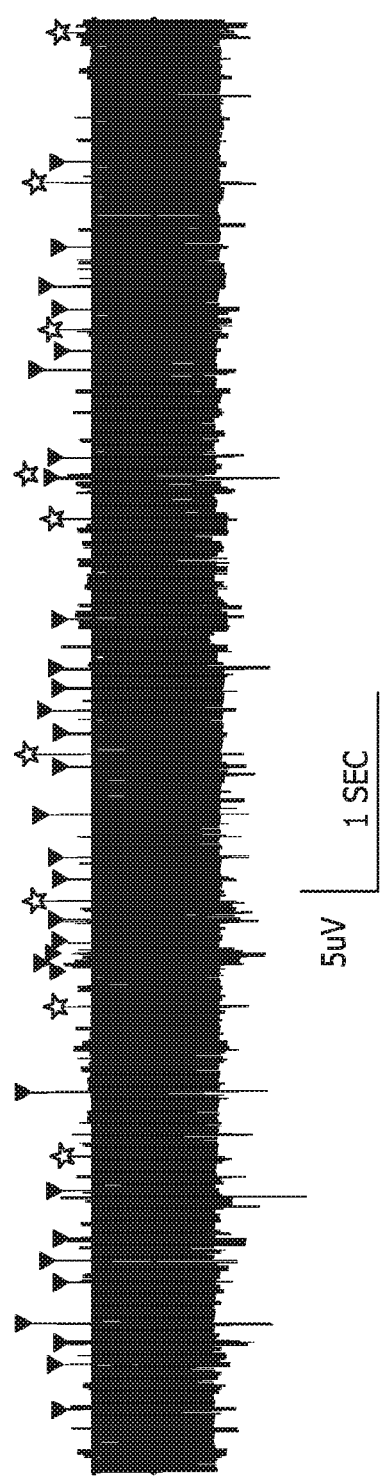
FIG. 7 shows 10 second samples of recordings within the tumor.
Figure 8:
FIG. 8 shows 10 second samples of recordings within the control.

In order to determine if there is neural activity within the solid breast tumor, differential recordings within the tumor and control were compared. An example of the activity recording from the one mouse is shown in FIGS. 7 and 8. Activity in the tumor is shown in FIG. 7 and large numbers of spikes each identified with + or small triangle are observed on top of a baseline noise. The activity recorded from the control side is shown in FIG. 8 and no spiking activity is observed.

Signals were obtained from seven mice were processed after implantation, until termination. (Mouse 032317_1, 062918A, 062917B all reached metastasis). FIGS. 9 and 10 show that the tumor activity was significantly higher (average over all mice: 112+/−46.5 spikes per 10 minutes) than the control activity (average over all mice: 3.3+/−2.6 spikes per 10 minutes).

Figure 11:
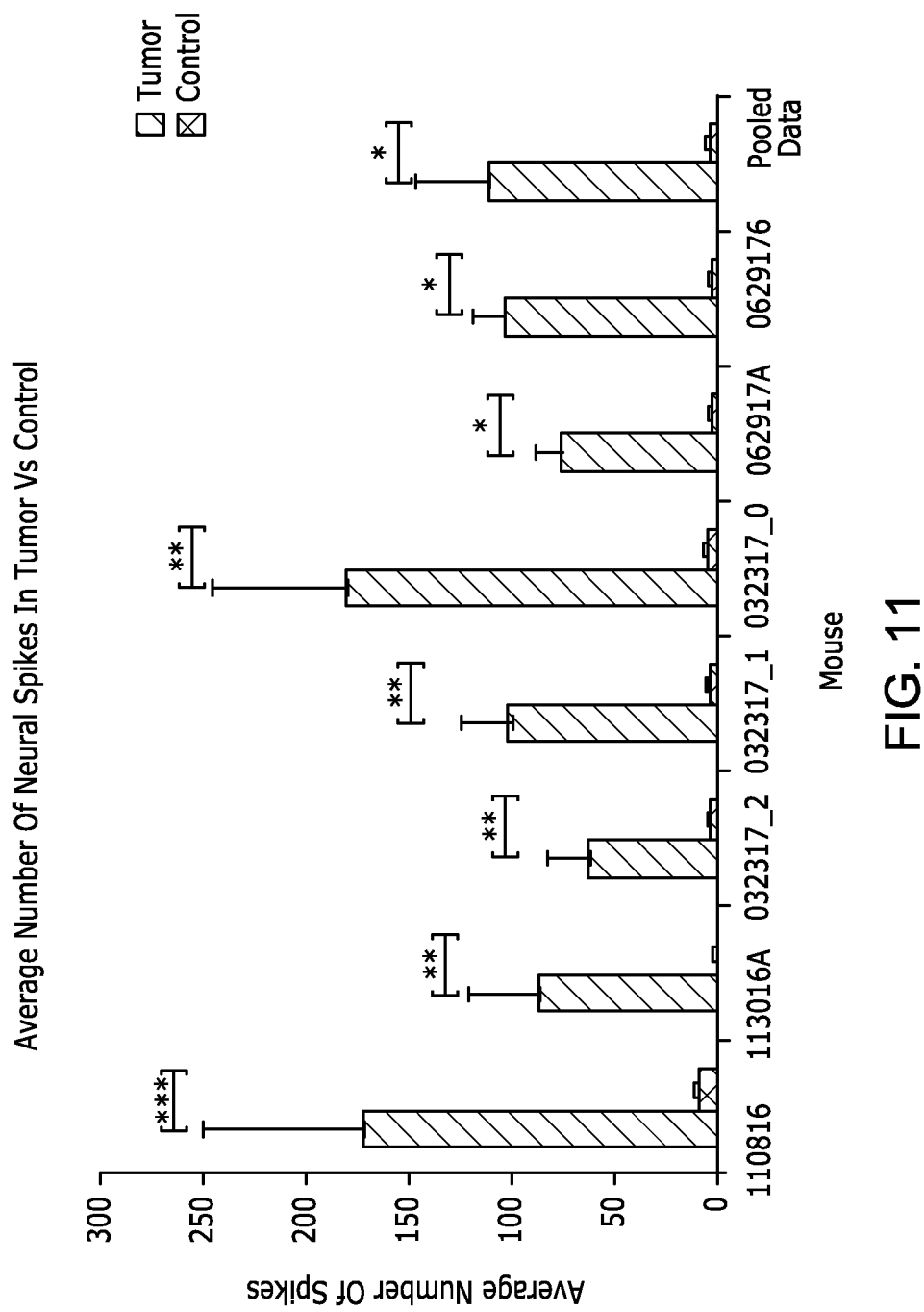
FIG. 11 shows a graph of the average number of spikes seen in the tumor and control for an average recording session in 7 mice.
Figures 14, 15:
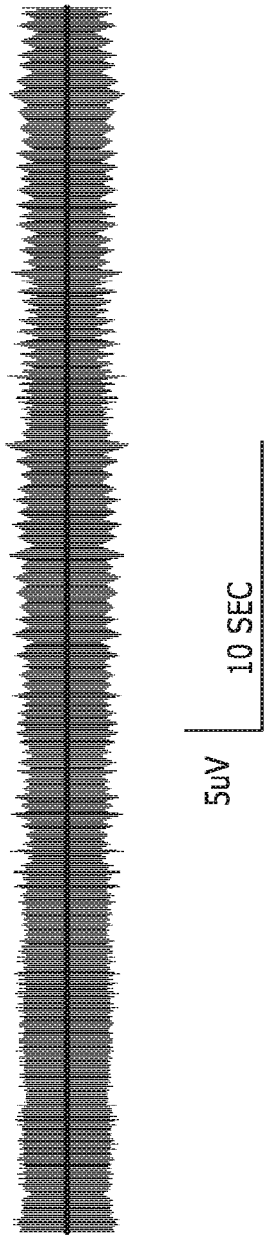
FIGS. 14-15 show neural activity within the control both before and after the injection of lidocaine.

The results of the spike counting in the control and tumor are statistically different from one another when analyzed with a t-Test: Paired Two Sample for Means; for the pooled data P(T<=t) one-tail=0.0001 the t-test results for all mice can be seen in the legend of FIG. 11 and indicate a significant difference. To determine that the sample size of seven mice was large enough to create statistically significant results, a power analysis test was performed. The power was 0.94 indicating a good sample set. The occasional activity above threshold seen in the control recordings is correlated to motion artifact as stated above. In order to test that this activity is the result of neural growth within metastatic tumors a lidocaine test was conducted.

Lidocaine Experiment

In order to demonstrate the recorded activity within the primary tumor was neural, Lidocaine was injected into the tumor core to block any neural action potentials within the recording proximity of the implanted electrodes.

A half an hour baseline recording was taken for each of the 5 mice. After the injection of (0.5 mL) of Lidocaine 2%, the high level of activity within the tumor ceased. A 30 minute recording was taken after injection. FIGS. 12-13 show that the neural spikes previously observed within the tumor (FIG. 12) are completely blocked by the addition of lidocaine (FIG. 13).

Following the addition of lidocaine, the baseline noise is also reduced significantly (from approximately 5 uV to ~1.5 uV). The remaining signal post injection is approximately equivalent to the thermal noise of the electrodes based on the following calculation:

Johnson Noise: $V(RMS) = \sqrt{4 * K_B * T * R * (F_2 - F_1)}$

Bandwidth$(F_2-F_1)$=20 KHz electrode resistance=5.6 KOhms

Temperature=37 Celsius $V(RMS)$=1.38 uV

This result indicates that the baseline noise is also neural in origin.

Figure 16:
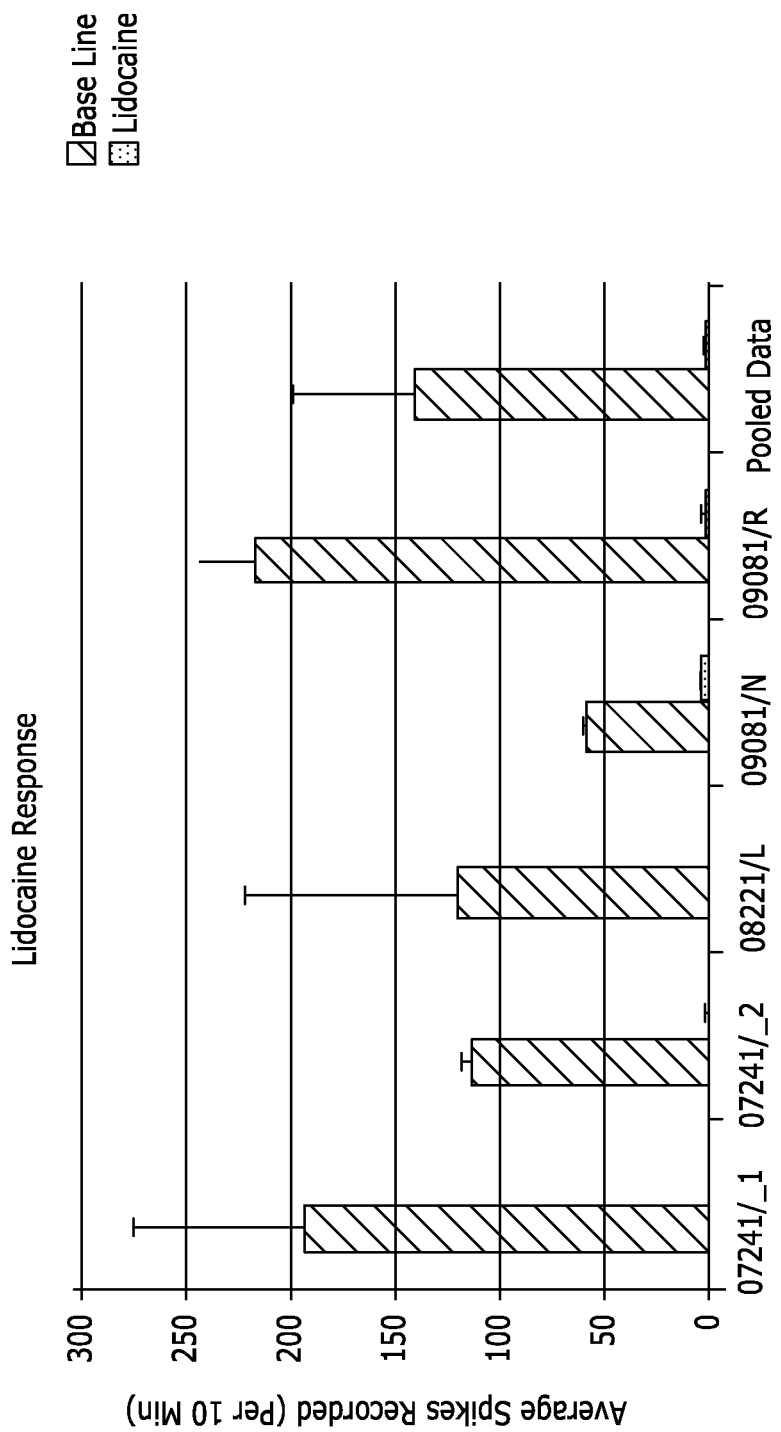
FIG. 16 shows a graph of the average spikes seen pre and post lidocaine injection of 5 mice.

Data for 5 mice are shown in FIG. 16. The 5 mice were at various stages of tumor growth (Mouse 072417_1, 090817N, and 090817R reached metastasis). The baseline activity was significantly higher in all of the mice (average over all mice: 140.3+/−62.7 spikes per 10 minutes) than after Lidocaine injection (average over all mice: 1.5+/−1.9 spikes per 10 minutes). The results of the spike counting pre and post lidocaine injection are statistically different when analyzed with a paired t-test (p<0.0001) with two-sample median test, on the average data of all mice. To determine that the sample size of five mice was large enough to create statistically significant results, a power analysis test was performed. The power was 0.94 indicating a good sample set.

Figure 17:
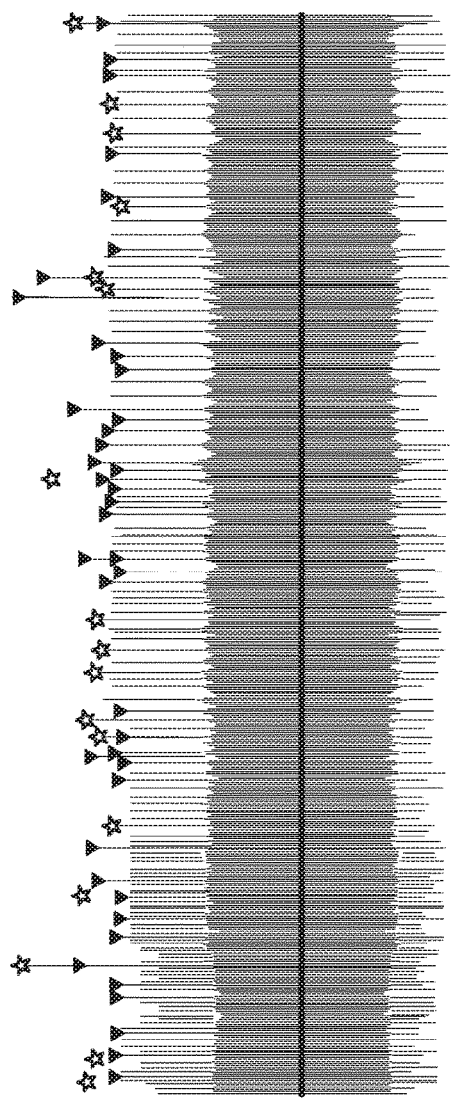
FIG. 17 shows the neural activity within the tumor before saline injection.
Figure 18:
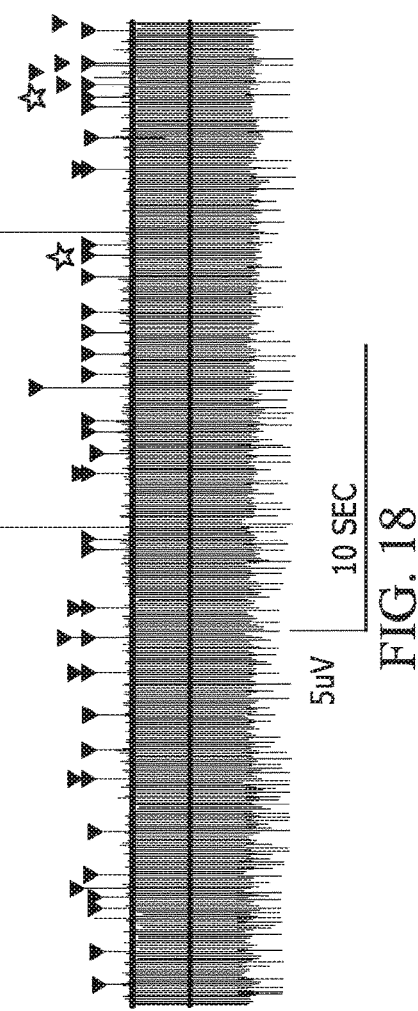
FIG. 18 shows the neural activity within the tumor after saline injection.
Figure 19:
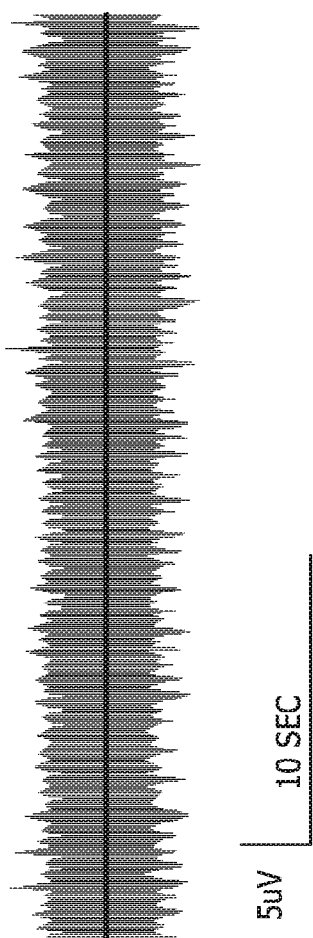
FIG. 19 shows the neural activity within the control before saline injection.
Figure 20:
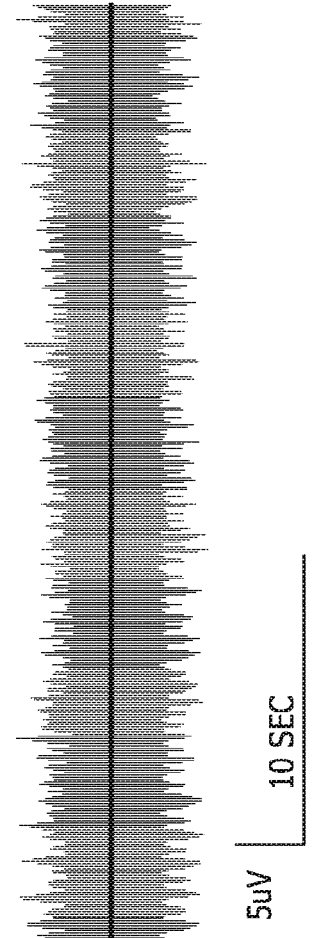
FIG. 20 shows the neural activity within the control after the saline injection.

This significant reduction in activity as a result of the lidocaine injection supports the hypothesis that electrical activity within the primary breast cancer tumor is of neural origin. To ensure this reduction in activity was not caused by a short-circuit in the implanted electrodes due to the injection process; a control trial was done where (0.5 mL) Saline was injected into the primary tumor. The results are shown in FIGS. 17 and 18 and confirm that saline injection does not block spiking activity in the tumor. The baseline recording, and post saline injection recordings are comparable to the previous baseline (pre lidocaine) recordings, thus supporting the hypothesis that nerve fibers are active within the primary breast cancer tumor. Data from the control group injected with lidocaine are shown in FIGS. 19 and 20 (pre and post, respectively).

Vagus Stimulation

To further test and define the activity within the tumor is neural, the vagus nerve was exposed and stimulated to determine if there is a connection between the parasympathetic nerve and the tumor growth.

Figure 21:
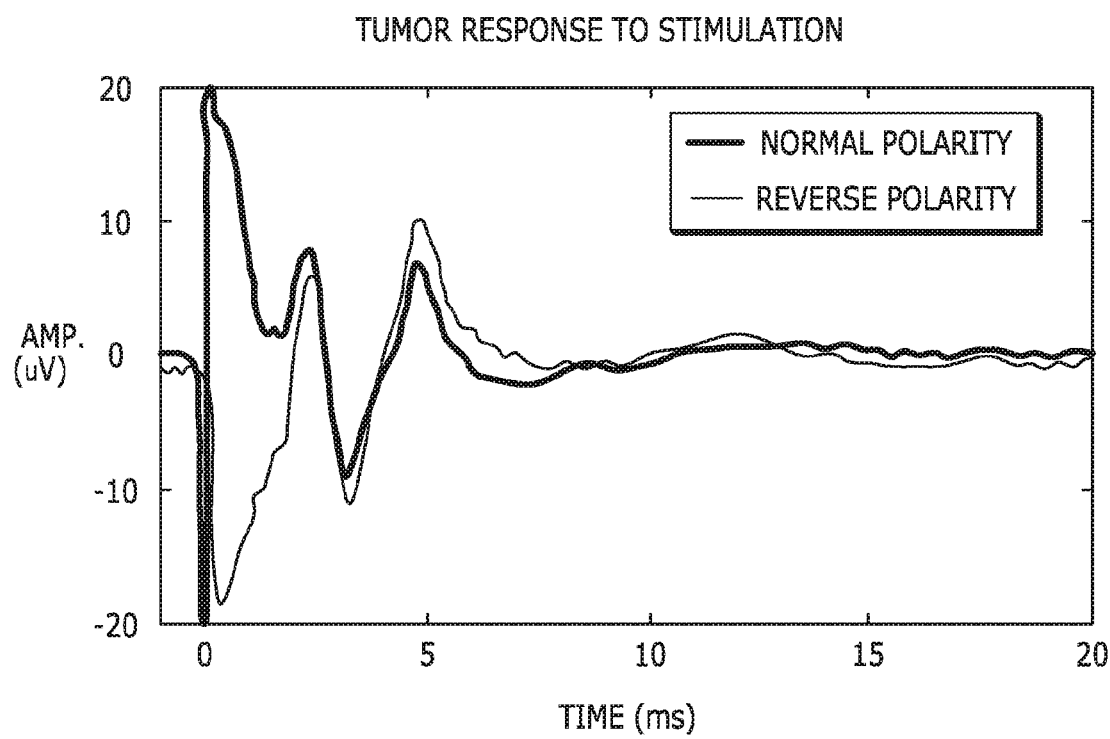
FIG. 21 shows the averaged response within the solid breast tumor to a 5 mA stimulation pulse applied to the vagus nerve in both forward and reverse polarity.
Figure 22:
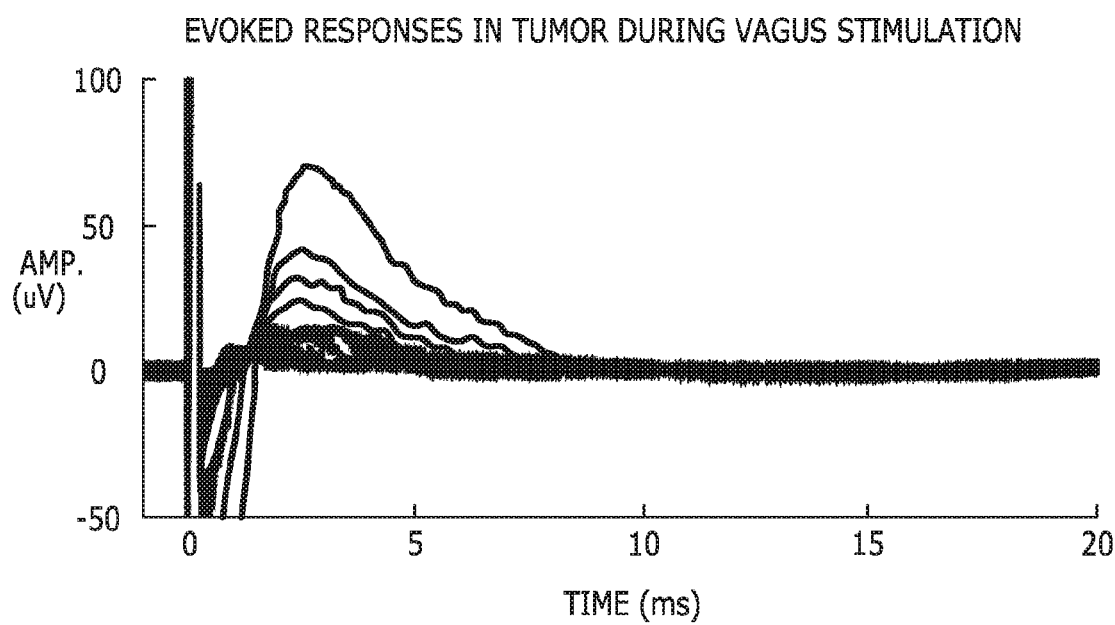
FIG. 22 shows raw neural response data for all stimulation pulses lined up and plotted on top of each other.

The experiment was performed on 2 mice, with 5 stimulation trials per mouse (results shown in FIGS. 21 and 22). In each trial, an evoked response in the tumor occurred during vagus stimulation. The response was present for both forward and reverse polarity of the stimulation, indicating the activity is neural and not an electrical artifact. The delay between the vagus stimulation and the tumor response was approximately 3 ms, which is the estimated time it would take for an unmyelinated axon potential traveling at 11.6 m/sec would need to travel the distance of approximately 3 cm to reach the tumor.

Histology

Histology was performed to determine any neural growth within the tumors as predicted by the neural recording experiments. Imaging of the immunostained slide was performed utilizing a confocal imaging microscope. Images of each stain type were taken (DAPI, TH, VACh-T, NF, GFP for the 4T1 cells). Neurofillaments, as well as Cholinergic and sympathetic nerve bundles containing fibers were observed and measured at approximately 30 to 50 μm in diameter.

The histology showed that axons are normally found in the advancing front of the tumor, and rarely in the tumor core, which correlates to the current theory in literature of axon recruitment. Together with the neural recordings, these results indicate that there are nerve fibers in tumors and that their activity can be recorded. These findings support the theory that the activity within the tumor is neural due to the presence of nerve fibers.

Neural Spikes Correlating to Metastasis

Next the neural recordings were examined in relation to the growth of the tumor using BLI to answer the following question: is the neural activing correlated with metastasis?

For each of the 5 mice recorded, the number of neural spikes was plotted vs number of days post inoculation. The mouse presented in FIG. 23 (CT090817R) is representative of all 5 specimens observed until metastasis where there is a clear increase in neural activity on the day metastasis as indicated by the appearance of tumors site in the lungs (day 22 in FIG. 24).

Figure 23:
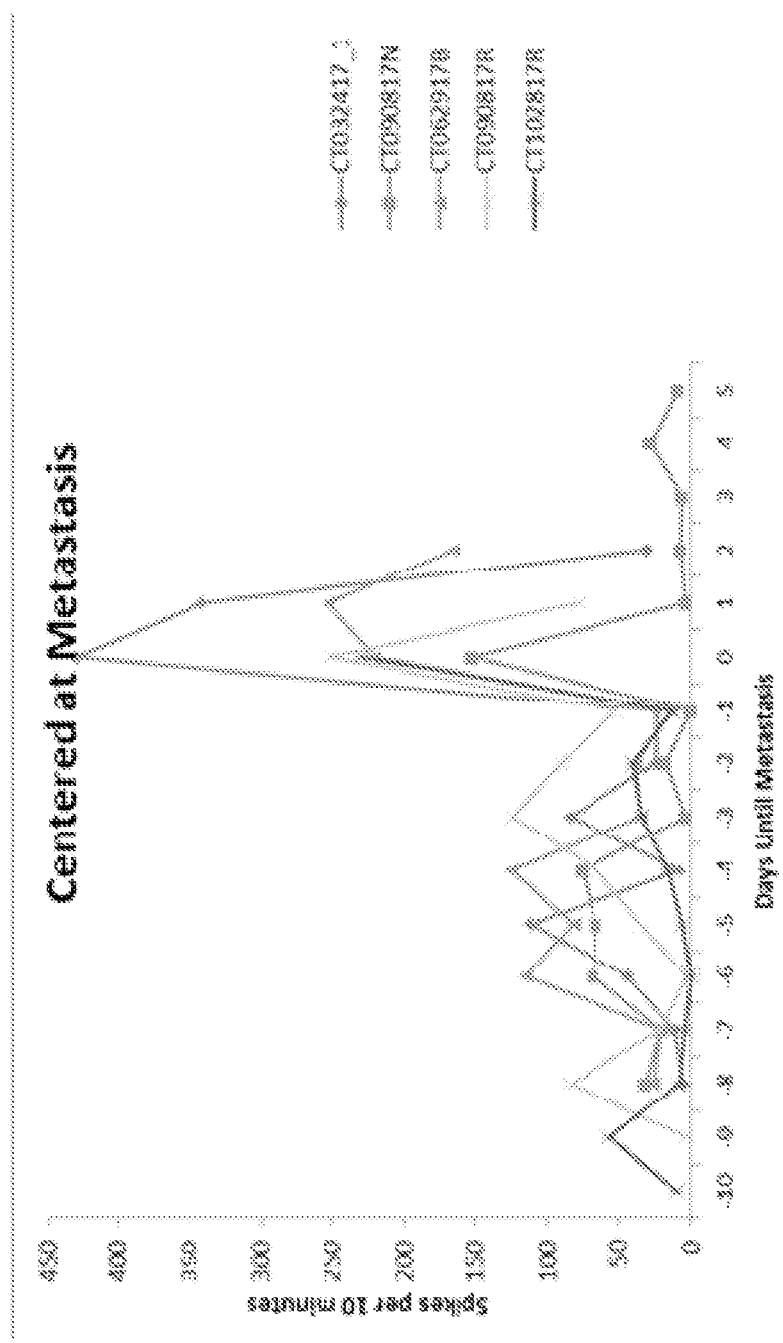
FIG. 23 shows a plot of the neural activity of 5 mice centered at metastasis to show the increase in neural activity observed.
Figure 24:
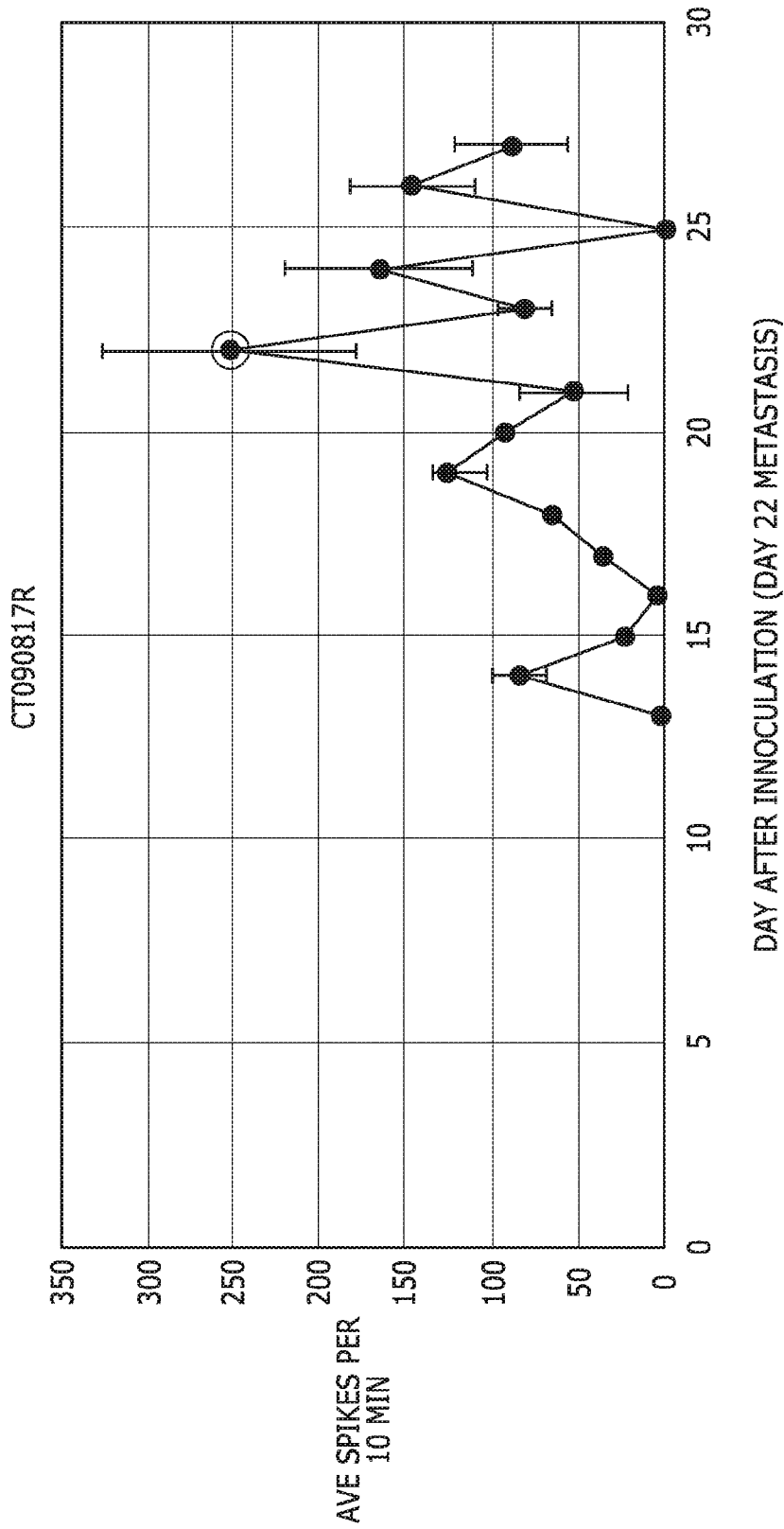
FIG. 24 shows a plot of the average number of spikes per day post inoculation.

To normalize these data from the various mice, the plots were centered on the day of metastasis (FIG. 23). The neural activity on the day of metastasis is 180%-500% increase of the firing rate of previous peak. The absolute number of spikes varies for each individual specimen, which is expected variations in the individual mouse, tumor growth, and electrode implantation. The paired t-test between day of metastasis and all other days was performed with all results showing statistically significant difference. The t-test values calculated for days before metastasis indicated no significant difference ($p>0.05$) except around the first peak of tumor growth (days −5 to −3).

Figure 25:
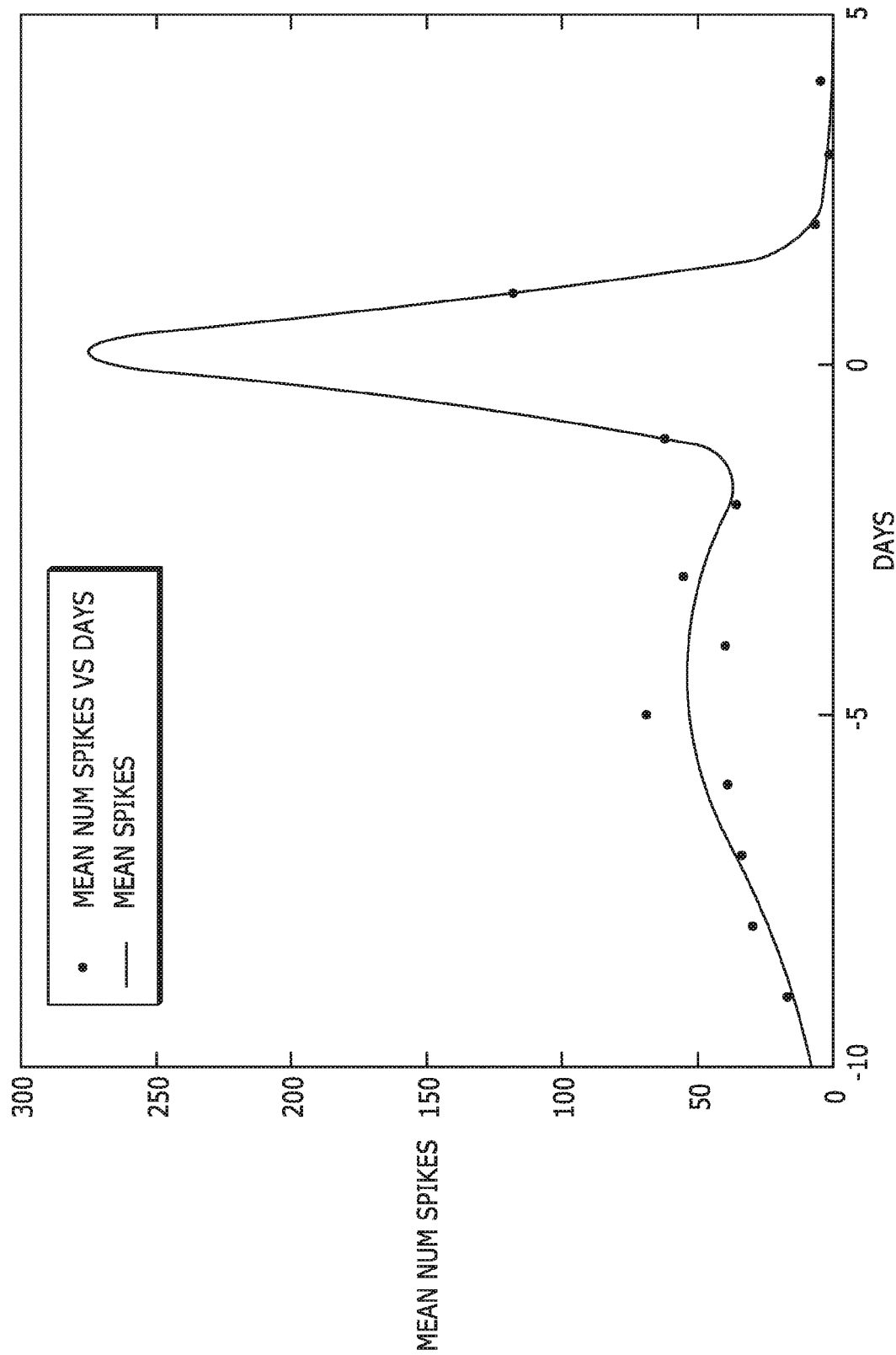
FIG. 25 shows a Gaussian fit to average neural spike data centered at metastasis.

To further analyze the findings, the data from all 5 mice were averaged and fitted to a Gaussian curve with two terms (FIG. 25). The R-squared value of the fit for the 5 mice ranged from 0.88 to 0.96 (with the average graph having a value of 0.94), indicating a good fit of this model. The Gaussian model shows that there is a clear correlation between neural activity and the occurrence of metastasis. In all mice analyzed: there was an initial increase in neural activity as the tumor grew, a decrease in activity 1.6 days on average before metastasis, and a 50-400% increase in activity during the metastasis event. As the Gaussian trend is consistent across all mice, the average regressive model can be utilized as a predictive aid for future experiments.

Neural Spike Analysis

Figure 26:
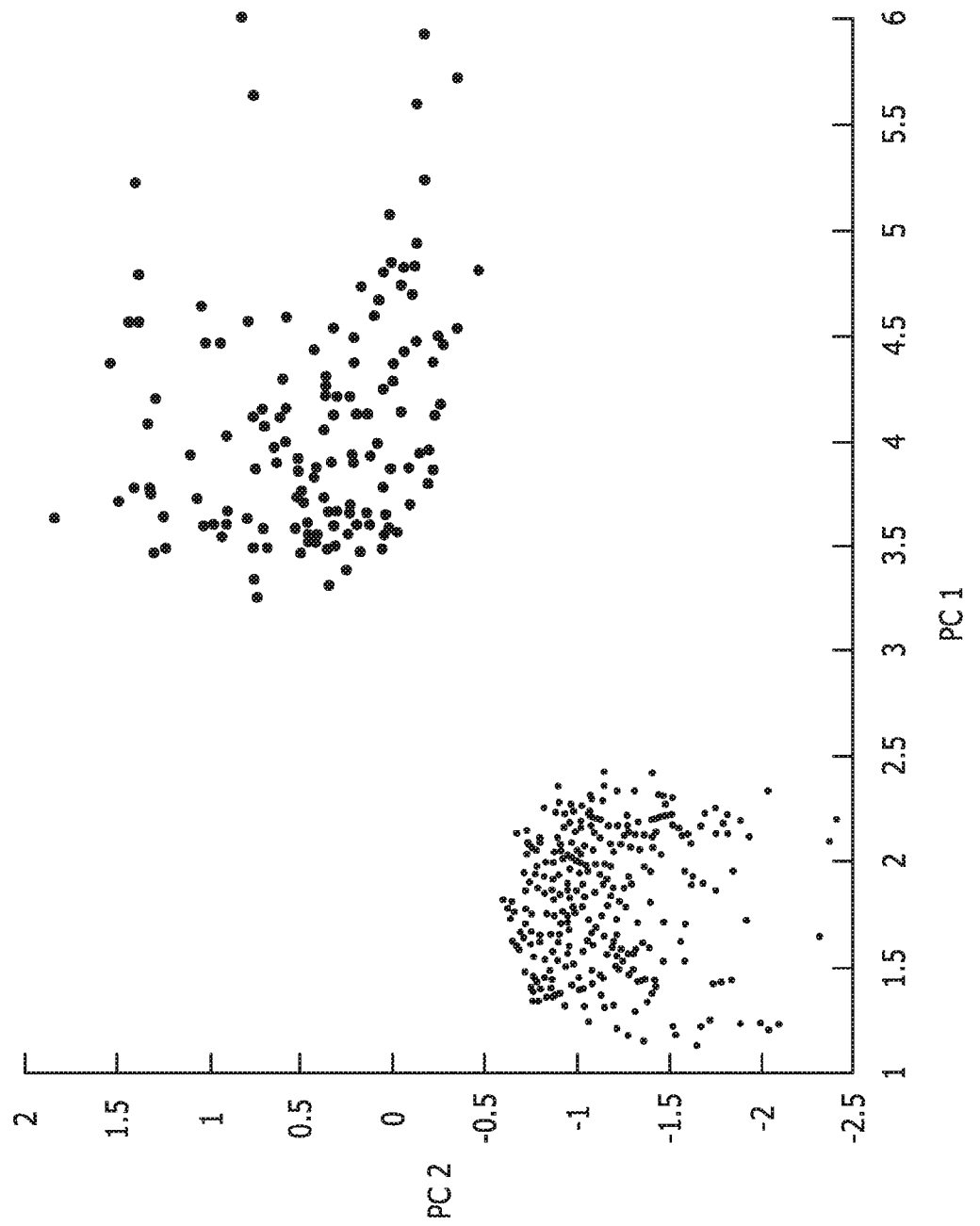
FIG. 26 shows a feature space representation of spike clusters showing the first two principle components.
Figure 27:
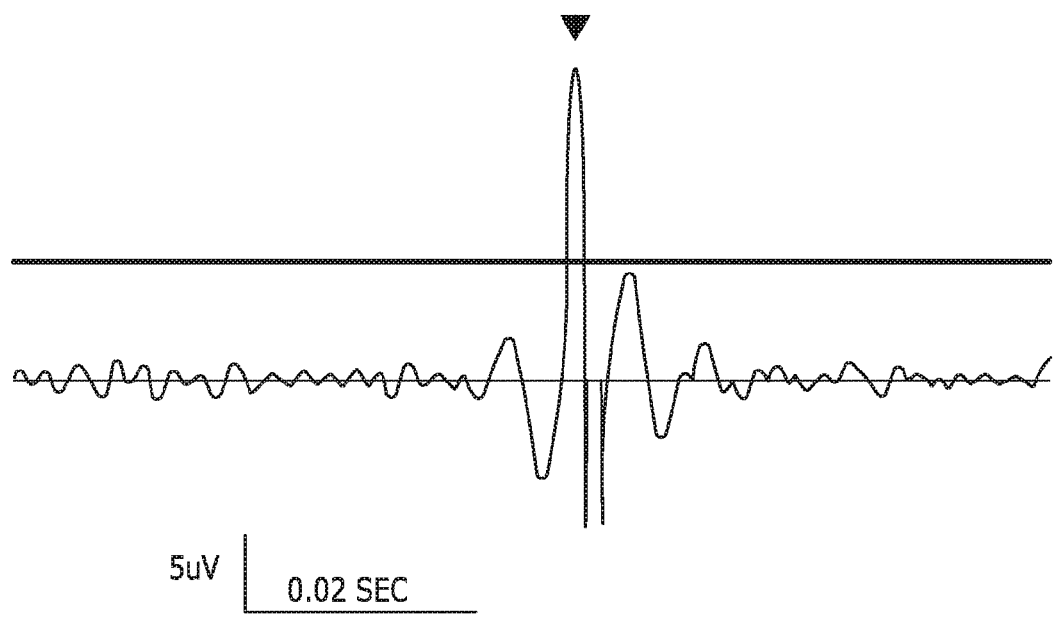
FIGS. 27-28 show representative spikes of identified neural clusters.
Figure 28:
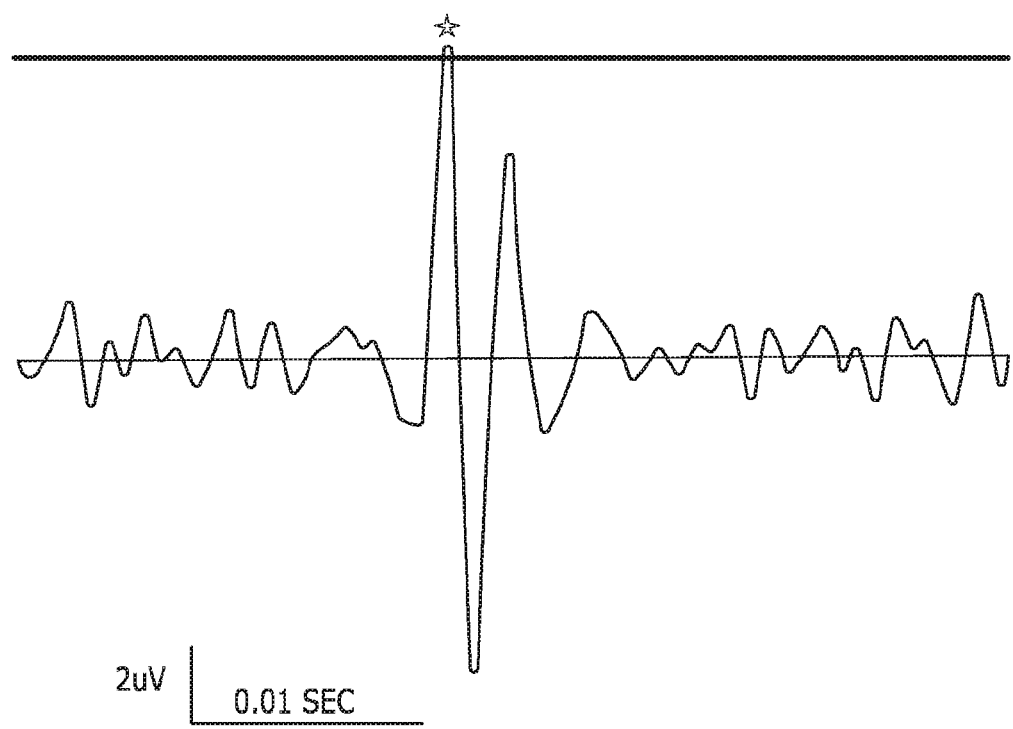

The UMS2K algorithm was used to identify the number of subgroups within the neural spikes. Two clusters were positively identified as different neural spike subgroups (FIG. 26). The Matlab spike sorting program further identified the characteristics of these two subgroups: a larger amplitude spike (10-20 mV) and a lower amplitude spike (<6 mV) (shown in FIGS. 27-28).

Figure 29:
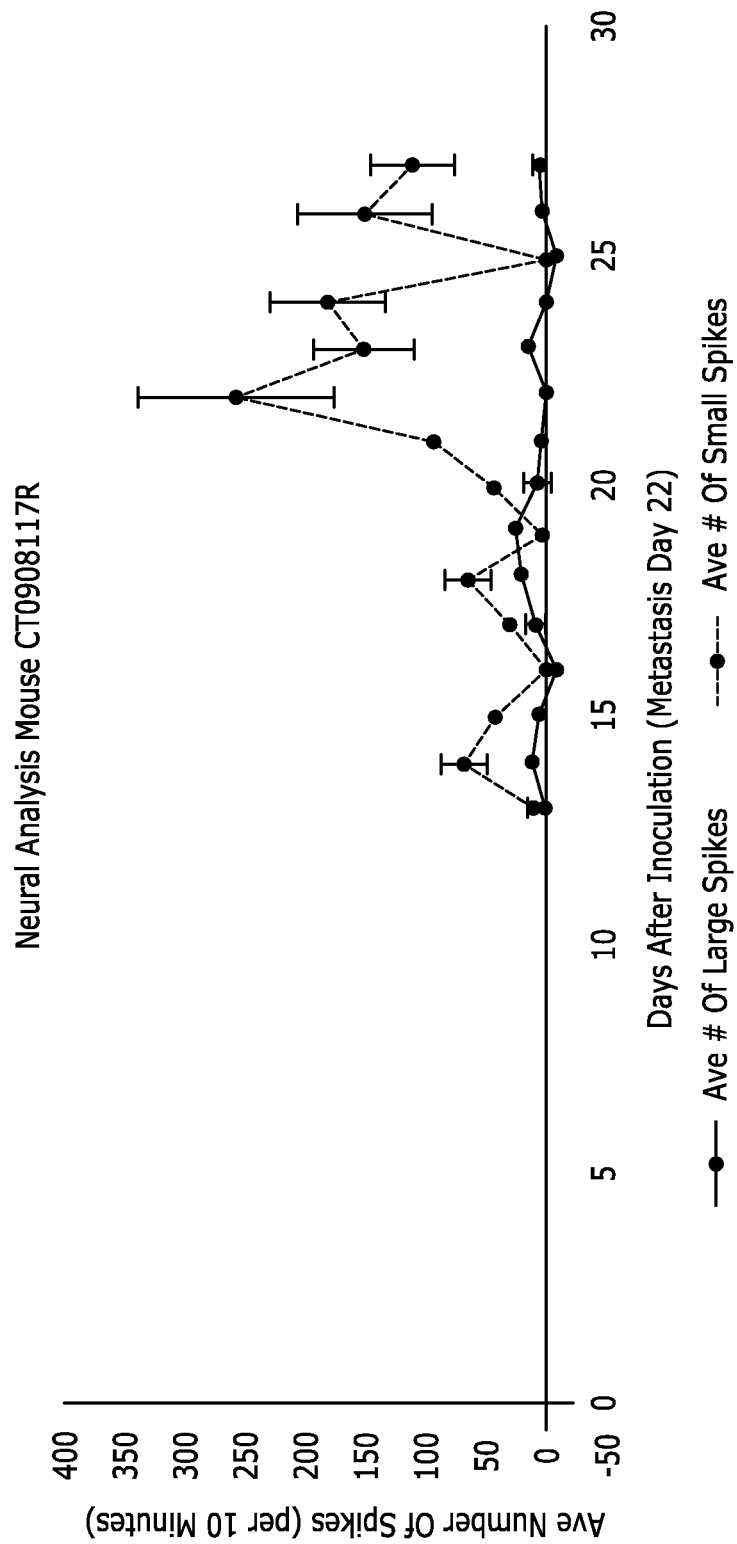
FIG. 29 shows a plot of the distribution of spike subgroups over time.

To determine the spike subgroups contribution to the overall neural activity during tumor growth and metastasis, both subgroup values were plotted on the same graph. The specimen (CT090817R) is utilized as a representative example. Considering the number of spikes in FIG. 29, the pattern of the smaller amplitude neural spikes correlates with the trend of total neural activity. The larger amplitude neural spikes remain at a constant low value throughout the entire trial.

The analysis of the width of the two types of spikes indicates no correlation to a metastatic or pre-metastatic event, it stays fairly consistent across all days of recording. The amplitude of the low amplitude neural spikes remains consistent across the entire trial. There is a gradual increase in the amplitude of the larger neural spikes several days before the metastasis event occurs. This increase could be used as a predictor of a future metastasis event.

Control Mice

In order to verify our hypothesis that neural activity is found exclusively in metastatic tumors, a non-metastatic triple negative mouse model was tested. The mice inoculated with D2A1 cells showed no activity above threshold in all recording trials. None of the D2A1 mice had a metastasis event occur during this experiment.

A paired t-test with two sample for means was performed on the average metastatic mouse data, vs. the non-metastatic mouse data in FIG. 25 to determine statistical difference. A one tailed p value of 0.0043 was calculated, indicating a significant difference between the two data sets.

From the above description, those skilled in the art will perceive improvements, changes and modifications. Such improvements, changes and modifications are within the skill of one in the art and are intended to be covered by the appended claims.

The following is claimed:

1. A method comprising:
implanting a recording device within a solid tumor or within a nerve that infiltrates the solid tumor;
directly measuring neural activity within the solid tumor, by the recording device, for a time;
receiving, by a system comprising a processor, the neural activity within the solid tumor for the time; and
determining, by the system, a state of the solid tumor based on the neural activity within the solid tumor, wherein the state is one of benign, malignant, or requires further testing.

2. The method of claim 1, when the state is malignant, further comprising comparing a property of a signal associated with the neural activity to a neural signal metric to predict a risk of growth and/or a risk of metastasis.

3. The method of claim 2, wherein the neural signal metric is based on a shape of the neural signal, a number and/or amplitude of spike events in the neural activity for the time, power, entropy, complexity, and/or mean number of crossings of the neural activity within the solid tumor for the time, and/or one or more frequency characteristics of the neural activity within the solid tumor for the time.

4. The method of claim 2, further comprising delivering a treatment to the solid tumor based on the risk of growth and/or a risk of metastasis.

5. The method of claim 4, wherein the treatment comprises delivering a pharmaceutical to the solid tumor, delivering a therapeutic agent to the solid tumor; delivering an immunotherapy to the solid tumor, stimulating neural activity to or from the tumor, blocking neural activity to or from the tumor, and/or delivering radiation to the solid tumor.

6. The method of claim 1, further comprising delivering a treatment to the solid tumor at a time based on comparing a property of a signal associated with the neural activity to a neural signal metric to determine the time for administering the treatment for optimal effect.

7. The method of claim 1, further comprising determining whether further diagnosis testing is required to determine whether the state is benign or malignant based on comparing a property of a signal associated with the neural activity.

8. The method of claim 1, wherein the neural activity is autonomic activity.

9. The method of claim 8, further comprising stimulating or blocking the autonomic activity based on the state.

10. A system comprising:
a recording electrode configured to be implanted within a solid tumor or within a nerve within a solid tumor and to record neural activity within the solid tumor for a time; and
a computing device comprising a non-transitory memory and a processor to receive the neural activity and determine a state of the solid tumor based on the neural activity within the solid tumor, wherein the state is one of benign, malignant, or requires further testing.

11. The system of claim 10, when the state is malignant, the processor further compares a property of a neural signal associated with the neural activity to a neural signal metric to predict a risk of growth and/or a risk of metastasis.

12. The system of claim 11, wherein the neural signal metric is based is based on a shape of the neural signal, a number and/or amplitude of spike events in the neural activity for the time, power, entropy, complexity, and/or mean number of crossings of the neural activity within the solid tumor for the time, and/or one or more frequency characteristics of the neural activity within the solid tumor for the time.

13. The system of claim 11, wherein the processor creates an output recommending delivery of a treatment to the solid tumor based on the risk of growth and/or a risk of metastasis.

14. The system of claim 13, wherein the treatment comprises delivering a pharmaceutical to the solid tumor, delivering a therapeutic agent to the solid tumor, delivering an immunotherapy to the solid tumor, stimulating neural activity to the tumor, blocking neural activity from the tumor, and/or delivering radiation to the solid tumor.

15. The system of claim 13, wherein the output comprises a time course for the treatment to be delivered based on the neural activity.

16. The system of claim 13, further comprising a treatment delivery device configured to perform the recommended delivery of the treatment to the solid tumor based on the output.

* * * * *